United States Patent
Yelle et al.

(10) Patent No.: US 6,174,902 B1
(45) Date of Patent: Jan. 16, 2001

(54) R-RABEPRAZOLE COMPOSITIONS AND METHODS

(75) Inventors: William E. Yelle, Littleton; Paul D. Rubin, Sudbury; Patrick Koch, Marlborough, all of MA (US)

(73) Assignee: Sepracor Inc., Marlborough, MA (US)

( * ) Notice: Under 35 U.S.C. 154(b), the term of this patent shall be extended for 0 days.

(21) Appl. No.: 09/301,196

(22) Filed: Apr. 28, 1999

Related U.S. Application Data

(60) Provisional application No. 60/083,725, filed on Apr. 30, 1998.

(51) Int. Cl.⁷ .................................................... A61K 43/40
(52) U.S. Cl. .............................................................. 514/338
(58) Field of Search ............................................... 514/338

(56) References Cited

U.S. PATENT DOCUMENTS

| | | | |
|---|---|---|---|
| 5,035,899 | 7/1991 | Saeki et al. | 424/480 |
| 5,045,552 | 9/1991 | Souda et al. | 514/338 |

FOREIGN PATENT DOCUMENTS

| | | |
|---|---|---|
| 0 585 722 A1 | 3/1994 | (EP) . |
| 0 645 140 A1 | 3/1995 | (EP) . |
| WO95/18612 | 7/1995 | (WO) . |
| WO96/01624 | 1/1996 | (WO) . |
| WO97/12580 | 4/1997 | (WO) . |
| WO97/25030 | 7/1997 | (WO) . |

OTHER PUBLICATIONS

Fijisaki et al, Abstract of Jpn J Pharmacol., vol. 76, pp. 279–88, Mar. 1998.*
Robinson et al, Abstract of Aliment Pharmacol Ther, vol. 11, pp. 973–80, Oct. 1997.*
Besancon et al, JBC, vol. 272, pp. 22348–22446, Sep. 1997.*
Prakash et al, Abstract of Drugs, vol. 55, pp. 261–7, Feb. 1998.*
Park et al, Abstract of Biol. Pharm. Bull., Bol. 19, pp. 182–7, Feb. 1996.*
VandenBranden et al. "Interaction of human liver cytochromes P450 in vitro with . . . " *Pharmacoqenetics* 6, 81–91 (1996).
Ishizaki et al. "Comparison of the interaction potential of a new proton pump . . . " *Clin. Pharm. Ther.* 58, 155–64 (1995).
Hirai et al. "A proton pump inhibitor, E3810, has antibacterial activity through . . . " *J. Gastroenterol* 30, 461–464 (1995).
Tomiyama et al. "Specific Proton Pump Inhibitors E3810 and Lansoprazole Affect . . . " *Biochem. Pharm.* 48, 2049–2055 (1994).
Yasuda et al. "Pharmacokinetic properties of E3810, a new proton pump inhibitor . . . " *Int. J. Clin. Pharm. Ther.* 32, 466–473 (1994).
Nochi et al. "Preparation and Absolute Configurations of Optical Isomers of Sodium . . . " *Chem. Pharm. Bull.* 44, 1853–1857 (1996).
Krusekopf et al. "Effects of benzimidazole derivatives on cytochrome P450 1A1 . . . " *Xenobiotica* 27, 1–9 (1997).
Tanaka et al. "A new model of delayed healing of acetic acid ulcers in rats by . . . " *Folia Pharmacologica Japonica* 110, 11–17 (1997) Abstract only.

* cited by examiner

*Primary Examiner*—James H. Reamer
(74) *Attorney, Agent, or Firm*—Heslin & Rothenberg, P.C.

(57) ABSTRACT

Methods and compositions are disclosed utilizing optically pure (+) rabeprazole for the treatment of ulcers in humans while substantially reducing the concomitant liability of adverse effects associated with the racemic mixture of rabeprazole. The optically pure (+) isomer is also useful for the treatment of gastroesophageal reflux. (+) Rabeprazole is an inhibitor of $H^+$ release and is therefore useful in the treatment of other conditions related to gastric hypersecretion such as Zollinger-Ellison Syndrome.

12 Claims, No Drawings

R-RABEPRAZOLE COMPOSITIONS AND METHODS

Cross Reference to Related Application

This application claims priority of U.S. Provisional Application 60/083,725 filed Apr. 30, 1998, the entire disclosure of which is incorporated herein by reference.

FIELD OF THE INVENTION

This invention relates to compositions of matter containing rabeprazole. The invention also relates to methods of treating and preventing ulcers, treating other conditions related to gastric hypersecretion, and treating psoriasis.

BACKGROUND OF THE INVENTION

Racemic rabeprazole is an orally active, potent, irreversible inhibitor of $H^+$, $K^+$-ATPase. The compound is one of the class of compounds known as gastric "proton pump" inhibitors. These compounds are weak organic bases which diffuse passively from the plasma into the acid-containing intracellular canaliculi of gastric parietal cells. At the low pH found in the lumen of these canaliculi, the protonated compounds rearrange to form pyridinium sulfenamides, which react with sulfhydryl groups present on the ATPase localized in the membranes lining the intracellular canaliculi. The alkylation of the sulfhydryl inhibits the ability of the enzyme to catalyze the secretion of $H^+$ into the lumen in exchange for $K^+$ ions. This inhibition results in an overall reduction in hydrochloric acid secretion by the parietal cells into the cavity of the stomach, thus increasing intragastric pH. As a consequence of reduced acidity in the stomach, the activity of the proteolytic enzyme pepsin is also markedly decreased. Because the proton pump is the final step in acid production and the compounds of this class combine covalently with the associated $H^+$, $K^+$-ATPase, a profound and prolonged inhibition of gastric acid secretion can be achieved.

Proton pump inhibitors have also been reported as useful in treating psoriasis. [See PCT application WO95/18612]

The $C_{max}$ of racemic rabeprazole is at about 4 to 5 hours in humans and the serum half-life is about 50 minutes to 1.5 hours depending on dose, but this does not reflect the duration of the acid inhibitory effect, which is about 24 hours. Racemic rabeprazole is comparable to omeprazole in its effects on hepatic drug metabolizing enzyme systems such as CYP 3A, although it appears to be less inhibitory of CYP 2C19 than is omeprazole and a more potent inducer of CYP 1A1 mRNA than is pantoprazole.

No cardiovascular or obvious physical changes have been so far reported in humans on administration of racemic rabeprazole, but reports of clinical trials are only recently beginning to appear. Most proton pump inhibitors produce significantly elevated fasting serum gastrin levels. This is cause for concern because prolonged elevated serum gastrin appears to be associated with diffuse and focal enterochromaffin-like cell hyperplasia and focal neoplasia (carcinoids) in rats. [Larsson et al. *Gastroenterology* 90, 391–399 (1986)]. Thus, despite its advantages, some adverse effects of racemic rabeprazole may remain, including, but not limited to, some incidence of hepatocellular neoplasia and gastric carcinoids on long-term therapy, and headache, diarrhea and skin alterations on acute therapy. It would therefore be particularly desirable to find a compound with the advantages of the racemic mixture of rabeprazole which would not have the aforementioned disadvantages.

SUMMARY OF THE INVENTION

This invention relates to the use of optically pure R(+) rabeprazole for treating ulcers of the stomach, duodenum and esophagus, gastroesophageal reflux diseases, Zollinger-Ellison Syndrome, and other disorders including those that would benefit from an inhibitory action on gastric acid secretion. R(+)Rabeprazole inhibits the $H^+$, $K^+$-ATPase associated with the gastric proton pump and the resulting secretion of gastric acid by parietal cells providing therapy in diseases associated with gastric hyperacidity. The invention also relates to a method of treating psoriasis using optically pure R(+) rabeprazole. Optically pure (+) rabeprazole provides this treatment while substantially reducing adverse effects, including, but not limited to, hepatocellular neoplasia, gastrin hypersecretion, gastric neoplasms or carcinoids, headache, diarrhea and skin alterations which are associated with the administration of the racemic mixture of rabeprazole.

The invention also relates to certain pharmaceutical compositions containing the R(+) isomer of rabeprazole.

DETAILED DESCRIPTION OF THE INVENTION

The active compound of these compositions and methods is an optical isomer of rabeprazole. The preparation of racemic rabeprazole is described in U.S. Pat. No. 5,045,552 and its equivalent European application 268956. Chemically, the active compound in the compositions and methods of the invention is the (+) isomer of 2-[[[4-(3-methoxypropoxy)-3-methyl-2-pyridinyl]methyl]sulfinyl-[1H]-benzimidazole(I), hereinafter referred to as (+)-rabeprazole.

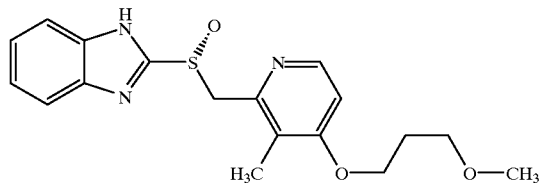

I (+) Rabeprazole, which is the subject of the present invention, is not presently commercially available.

The separation of racemic rabeprazole into R(+) rabeprazole and S(−) rabeprazole by chromatography has been described by Nochi et al [*Chem. Pharm. Bull.* 44, 1853–1857 (1996)], but the pharmacology and pharmacodynamics have not been described for either enantiomer. In addition to the chromatographic separation of the racemate into its enantiomers, asymmetric oxidation of the thioether precursor and bioreduction of the racemate to eliminate the S(−) enantiomer can be carried out in analogous fashion to the procedure described for lansoprazole in PCT applications WO 9602535 and 9617077; the disclosures of both are incorporated herein by reference.

It has now been discovered that the optically pure (+) isomer of rabeprazole is a superior agent for treating ulcers of the stomach, duodenum and esophagus, gastroesophageal reflux diseases, Zollinger-Ellison Syndrome, psoriasis and other disorders, including those that would benefit from an inhibitory action on $H^+$, $K^+$-ATPase in that it provides this effective treatment while substantially reducing the adverse effects of racemic rabeprazole including, but not limited to, hepatocellular neoplasia, gastric carcinoids, headache, diarrhea and skin alterations. The R(+) isomer of rabeprazole is also a superior agent for treating ulcers and other disorders by virtue of the greater predictability of dosage among patients, as discussed below.

The present invention encompasses a method of treating ulcers, which comprises administering to a human in need of such therapy, an amount of (+) rabeprazole, or a pharmaceutically acceptable salt thereof, substantially free of its (−) stereoisomer, said amount being sufficient to alleviate the symptoms of ulcers. The method substantially reduces the concomitant liability of adverse effects associated with the administration of the racemic compound by providing an amount which is insufficient to cause the adverse effects associated with the racemic mixture of rabeprazole.

The present invention also encompasses an oral antiulcer composition for the treatment of a human in need of antiulcer therapy, which comprises a pharmaceutically acceptable carrier for oral administration and a therapeutically effective amount of (+) rabeprazole, or a pharmaceutically acceptable salt thereof, substantially free of its (−) stereoisomer. Preferably the composition is in the form of a tablet or capsule and the amount of (+) rabeprazole in the tablet or capsule is 10, 30 or 50 mg.

The present invention further encompasses a method of treating gastroesophageal reflux disease and of treating conditions caused by or contributed to by gastric hypersecretion. Conditions associated with hypersecretion in humans may include, but are not limited to, Zollinger-Ellison syndrome.

The present invention further encompasses a method of treating psoriasis while substantially reducing the adverse effects of racemic rabeprazole.

Utilizing the optically pure or substantially optically pure isomer of (+) rabeprazole results in enhanced efficacy, diminished adverse effects, and accordingly, an improved therapeutic index. Moreover, the R(+) enantiomer provides a desirable half-life and shows less variation in the patient population between so-called extensive metabolizers and poor metabolizers than does racemic rabeprazole. It is therefore, more desirable to use the (+) isomer of rabeprazole than to administer the racemic mixture because predictability of an effective and safe dose for an individual patient is greater.

The term "adverse effects" includes, but is not limited to, hepatocellular neoplasia, gastrin hypersecretion, gastric carcinoids, headache, diarrhea and skin alterations.

The term "substantially free of its (−) stereoisomer" as used herein means that the compositions contain at least 90% by weight of (+) rabeprazole and 10% by weight or less of (−) rabeprazole. In a more preferred embodiment the term "substantially free of the (−) isomer" means that the composition contains at least 99% by weight of (+) rabeprazole, and 1% or less of (−) rabeprazole. These percentages are based upon the total amount of rabeprazole in the composition. The terms "substantially optically pure (+) isomer of rabeprazole" or "substantially optically pure (+) rabeprazole" and "optically pure (+) isomer of rabeprazole" and "optically pure (+) rabeprazole" are also encompassed by the above-described amounts.

The term "treating ulcers" as used herein means treating, alleviating or palliating such conditions, and thus providing relief from the symptoms of nausea, heartburn, post-prandial pain, vomiting, and diarrhea.

The term "a method for treating gastroesophageal reflux diseases in a human" as used herein means treating, alleviating or palliating the conditions that result from the backward flow of the stomach contents into the esophagus.

The term "treating a condition caused, or contributed to, by gastric hypersecretion in a human" as used herein means treating, alleviating or palliating such disorders associated with hypersecretion, thus providing relief from the symptoms of the aforementioned conditions. Zollinger-Ellison Syndrome is among the conditions caused by or contributed to by hypersecretion.

The term "treating psoriasis" as used herein means treating, alleviating or palliating the condition, and thus providing relief from the symptoms of pruritis, epidermal scaling, itching and burning.

The magnitude of a prophylactic or therapeutic dose of (+) rabeprazole in the acute or chronic management of disease will vary with the severity of the condition to be treated and the route of administration. The dose and perhaps the dose frequency will also vary according to the age, body weight and response of the individual patient. In general, the total daily dose range for (+) rabeprazole for the conditions described herein is from about 5 mg to about 200 mg in single or divided doses. Preferably a daily dose range should be about 10 mg to about 50 mg in single or divided doses. In managing the patient, the therapy should be initiated at a lower dose, perhaps at about 10 mg to about 15 mg and increased up to about 50 mg or higher depending on the patient's global response. It is further recommended that children and patients over 65 years and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The terms "an amount sufficient to alleviate or palliate ulcers but insufficient to cause said adverse effects," "an amount sufficient to alleviate the symptoms of gastroesophageal reflux but insufficient to cause said adverse effects," "an amount sufficient to alleviate gastric hypersecretion but insufficient to cause said adverse effects" and "an amount sufficient to treat psoriasis" are encompassed by the above-described dosage amounts and dose frequency schedule.

The relative activity, potency and specificity of optically pure rabeprazole and racemic rabeprazole both as gastric antisecretory agents and plasma gastrin elevating agents can be determined by a pharmacological study in animals according to the method of Decktor et al. [*J. Pharmacol. Exp. Ther.* 249, 1–5 (1989)]. The test provides an estimate of relative activity, potency and, through a measure of specificity, an estimate of therapeutic index. Fasted rats, implanted with a gastric cannula, receive single oral or parenteral doses of (+) rabeprazole, (−) rabeprazole or racemate, 1 hour before collection of gastric juice over a four hour period. Acid output and pH are then determined on each sample. Dose response evaluations are performed with each compound to determine the lowest dose which inhibits acid output by at least 95% and maintains gastric pH above 7.0. Plasma gastrin levels are then determined in a second group of rats treated with the doses selected in the first series of tests. Blood samples are taken for analyses over the five hour period after dosing, and both peak level as well as area-under-the-curve analyses of the gastrin responses are made. These responses are then analyzed statistically using Student's "t" test to assess whether equivalent antisecretory doses show differences in gastrin responses.

Any suitable route of administration may be employed for providing the patient with an effective dosage of (+) rabeprazole. Rectal, parenteral (subcutaneous, intramuscular, intravenous), transdermal, and like forms of administration are possible, but oral administration is preferred. Oral dosage forms include tablets, troches, dispersions, suspensions, solutions, capsules, and the like.

The pharmaceutical compositions of the present invention comprise (+) rabeprazole as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic bases. Since the compound of the present invention is a weak acid and is unstable at low pH, salts may be prepared from pharmaceutically acceptable non-toxic bases including inorganic and organic bases. Suitable pharmaceutically acceptable base addition salts for the compound of the present invention include metallic salts of aluminum, calcium, lithium, magnesium, potassium, sodium, titanium and zinc or organic salts made from lysine, N,N'-dibenzylethylenediamine, chloroprocaine, choline, diethanolamine, ethylenediamine, meglumine (N-methylglucamine) and procaine. Sodium salts are preferred.

The compositions of the present invention include suspensions, solutions, elixirs or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. It has been found that the inclusion of mannitol and of basic salts of calcium and magnesium in the compositions allows the preparation of tablets and capsules that retain good stability. If desired, tablets and granules may be coated by standard aqueous or nonaqueous techniques. Oral dosage forms suitable for rabeprazole are described in U.S. Pat. No. 5,035,899 and in PCT applications WO96/01624, WO97/12580 and WO97/25030, the disclosures of which are incorporated herein by reference.

In addition to the common dosage forms set out above, the compounds of the present invention may also be administered by controlled release formulations, which are well known in the art. Compositions suitable for rectal administration are described in European Application 645140, the disclosure of which is incorporated herein by reference.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent. Desirably, each tablet contains from about 10 mg to about 100 mg of the active ingredient, and each cachet or capsule contains from about 10 mg to about 100 mg of the active ingredient. Most preferably, the tablet, cachet or capsule contains either one of three dosages, about 10 mg, about 30 mg or about 50 mg of (+) rabeprazole for oral administration.

The invention is further defined by reference to the following examples describing in detail the preparation of the compositions of the present invention, as well as their utility. It will be apparent to those skilled in the art that many modifications, both to materials and methods, may be practiced without departing from the purpose and interest of this invention.

EXAMPLES

Example 1 - Tablets
Composition per tablet:

| | |
|---|---|
| R(+) rabeprazole | 30 mg |
| Precipitated calcium carbonate | 50 mg |
| Corn Starch | 40 mg |
| Lactose | 73.4 mg |
| Hydroxypropylcellulose | 6 mg |
| Magnesium stearate | (0.05 ml) |
| Total | 200.0 mg |

Example 1

R(+) Rabeprazole, precipitated calcium carbonate, corn starch, lactose and hydroxypropylcellulose are mixed together, water is added, and the mixture is kneaded, then dried in vacuum at 40° C. for 16 hours, ground in a mortar and passed through a 16-mesh sieve to give granules. To this is added magnesium stearate and the resultant mixture is made up into tablets each weighing 200 mg on a rotary tableting machine.

Example 2 - Granules
Composition per tablet:

| | |
|---|---|
| R(+) rabeprazole | 30 mg |
| Magnesium carbonate | 20 mg |
| Corn Starch | 80 mg |
| Microcrystalline cellulose | 20 mg |
| Carboxymethylcellulose calcium | 10 mg |
| Hydroxypropylcellulose | 10 mg |
| Pluronic F68 | 4 mg |
| Lactose | 26 mg |
| Water | (0.05 ml) |
| Total | 200 mg |

Example 2

The ingredients above are mixed well in the proportions shown, water is added, and the mixture is kneaded and granulated in an extruder granulator (screen size 1.0 mm φ). The granules are immediately converted to spherical form in a spheronizer. The spherical granules are then dried under vacuum at 40° C. for 16 hours and passed through round sieves to give 12- to 42-mesh granules.

| Example 3 - Capsules | |
|---|---|
| Enteric coating composition: | |
| Eudragit L-30D | 138 mg (solids 41.4 mg) |
| Talc | 4.1 mg |
| Polyethylene glycol | |
| 5000 | 12.4 mg |
| Tween 80 | 2.1 mg |
| Water | 276 µl |
| Composition of enteric granules: | |
| Granules of Example 5 | 200 mg |
| Enteric coat | 60 mg |
| Total | 260 mg |
| Composition per capsule: | |
| Enteric granules | 260 mg |
| No. 1 hard capsule | 76 mg |
| Total | 336 mg |

Example 3

Enteric granules are produced by coating the granules obtained in Example 2 with the enteric coating composition shown using a fluidized bed granulator under conditions such that the inlet air temperature is 50° C. and the granule temperature is about 40° C. Number 1 hard capsules are filled with the enteric granules thus obtained in an amount of 260 mg per capsule using a capsule filling machine.

An enteric coating, such as the polyacrylate Eudragit L® and Eudragit S® series, is applied by spray coating the tablets, preferably with an aqueous dispersion of the coating polymer. Tablets of other strengths may be prepared by altering the ratio of active ingredient to the excipients or to the final weight of the tablet.

What is claimed is:

1. A method of treating ulcers which comprises administering to a human a therapeutically effective amount of optically pure R(+)isomer of rabeprazole, or a pharmaceutically acceptable salt thereof.

2. A method of treating gastroesophageal reflux disease which comprises administering to a human a therapeutically effective amount of optically pure R(+)isomer of rabeprazole, or a pharmaceutically acceptable salt thereof.

3. A method of treating a condition caused by or contributed to by gastric hypersecretion which comprises administering to a human a therapeutically effective amount of optically pure R(+)isomer of rabeprazole, or a pharmaceutically acceptable salt thereof.

4. The method according to claim 3 wherein said condition is Zollinger-Ellison Syndrome.

5. A method of treating psoriasis which comprises administering to a human a therapeutically effective amount of optically pure R(+)isomer of rabeprazole, or a pharmaceutically acceptable salt thereof.

6. The method of claim 1 wherein (+) rabeprazole is administered orally.

7. The method of claim 6 wherein the amount of (+) rabeprazole or a pharmaceutically acceptable salt thereof administered is from about 5 mg to about 200 mg per day.

8. The method of claim 7 wherein the amount administered is from about 10 mg to about 50 mg per day.

9. The method of claim 1 wherein the amount of (+) rabeprazole or a pharmaceutically acceptable salt thereof is greater than approximately 90% by weight of the total weight of rabeprazole.

10. The method of claim 1 wherein the amount of (+) rabeprazole or a pharmaceutically acceptable salt thereof is greater than approximately 99% by weight of the total weight of rabeprazole.

11. A pharmaceutical composition comprising a pharmaceutically acceptable carrier for oral therapy and a therapeutically effective amount of (+) rabeprazole or a pharmaceutically acceptable salt thereof, substantially free of its (−) stereoisomer.

12. A pharmaceutical composition according to claim 11 in the form of a tablet or capsule.

* * * * *